US010537740B2

(12) United States Patent
Carbunaru et al.

(10) Patent No.: US 10,537,740 B2
(45) Date of Patent: *Jan. 21, 2020

(54) CHARGE RECOVERY BI-PHASIC CONTROL FOR TISSUE STIMULATION

(71) Applicant: Boston Scientific Neuromodulation Corporation, Valencia, CA (US)

(72) Inventors: Rafael Carbunaru, Valley Village, CA (US); Kerry Bradley, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 405 days.

This patent is subject to a terminal disclaimer.

(21) Appl. No.: 15/234,866

(22) Filed: Aug. 11, 2016

(65) Prior Publication Data

US 2016/0346550 A1    Dec. 1, 2016

Related U.S. Application Data

(63) Continuation of application No. 12/938,202, filed on Nov. 2, 2010, now Pat. No. 9,415,223.

(Continued)

(51) Int. Cl.
*A61N 1/36* (2006.01)
*A61N 1/05* (2006.01)

(52) U.S. Cl.
CPC ....... *A61N 1/36128* (2013.01); *A61N 1/0551* (2013.01); *A61N 1/36125* (2013.01);
(Continued)

(58) Field of Classification Search
CPC ............ A61N 1/36071; A61N 1/36128; A61N 1/0531; A61N 1/0551; A61N 1/36125; A61N 1/36185; A61N 1/36178
(Continued)

(56) References Cited

U.S. PATENT DOCUMENTS 6,393,225 B1    5/2002   Yamada
6,516,227 B1*   2/2003   Meadows ............ A61N 1/0553
                                                    607/117

(Continued)

OTHER PUBLICATIONS

"U.S. Appl. No. 12/938,202, Advisory Action dated Mar. 12, 2014", 7 pgs.

(Continued)

*Primary Examiner* — Christopher Koharski
*Assistant Examiner* — Pamela M. Bays
(74) *Attorney, Agent, or Firm* — Schwegman Lundberg & Woessner, P.A.

(57) ABSTRACT

A method and external control device for providing therapy to a patient using first and second electrodes implanted within the patient is provided. A train of electrical multi-phasic pulses is generated. A first electrical current is sourced from the second electrode and at least a portion of the first electrical current is sunk to the first electrode during a stimulation phase of each multi-phasic pulse, thereby therapeutically stimulating a first tissue region adjacent the first electrode. A second electrical current is sourced from the first electrode and at least a portion of the second electrical current is sunk to the second electrode during a charge recovery phase of each multi-phasic pulse, thereby recovering at least a portion of the charge that had been injected into the patient during the stimulation phase of each multi-phasic pulse, and therapeutically stimulating a second tissue region adjacent the second electrode.

19 Claims, 10 Drawing Sheets

Related U.S. Application Data

(60) Provisional application No. 61/257,279, filed on Nov. 2, 2009.

(52) U.S. Cl.
CPC ...... *A61N 1/36178* (2013.01); *A61N 1/36071* (2013.01); *A61N 1/36185* (2013.01)

(58) Field of Classification Search
USPC .................................................... 607/72
See application file for complete search history.

(56) References Cited

U.S. PATENT DOCUMENTS

| | | | |
|---|---|---|---|
| 6,895,280 | B2 | 5/2005 | Meadows et al. |
| 6,993,384 | B2 | 1/2006 | Bradley et al. |
| 7,650,184 | B2 | 1/2010 | Walter |
| 8,019,439 | B2 | 9/2011 | Kuzma et al. |
| 9,415,223 | B2 | 8/2016 | Carbunaru et al. |
| 2003/0114899 | A1 | 6/2003 | Woods et al. |
| 2003/0236558 | A1* | 12/2003 | Whitehurst .......... A61N 1/0556 607/45 |
| 2007/0043392 | A1 | 2/2007 | Gliner et al. |
| 2007/0135868 | A1* | 6/2007 | Shi .................... A61N 1/36071 607/62 |
| 2007/0142863 | A1 | 6/2007 | Bradley |
| 2007/0168004 | A1 | 7/2007 | Walter |
| 2007/0168007 | A1 | 7/2007 | Kuzma et al. |
| 2010/0121409 | A1 | 5/2010 | Kothandaraman et al. |
| 2011/0106214 | A1 | 5/2011 | Carbunaru et al. |

OTHER PUBLICATIONS

"U.S. Appl. No. 12/938,202, Advisory Action dated Jun. 30, 2015", 11 pgs.
"U.S. Appl. No. 12/938,202, Appeal Brief filed May 16, 2014", 18 pgs.
"U.S. Appl. No. 12/938,202, Final Office Action dated Jan. 16, 2014", 14 pgs.
"U.S. Appl. No. 12/938,202, Final Office Action dated Feb. 27, 2015", 17 pgs.
"U.S. Appl. No. 12/938,202, Non Final Office Action dated Jun. 26, 2013", 13 pgs.
"U.S. Appl. No. 12/938,202, Non Final Office Action dated Sep. 10, 2014", 23 pgs.
"U.S. Appl. No. 12/938,202, Non Final Office Action dated Nov. 16, 2015", 19 pgs.
"U.S. Appl. No. 12/938,202, Notice of Allowance dated Apr. 12, 2016", 8 pgs.
"U.S. Appl. No. 12/938,202, Response filed Feb. 16, 2016 to Non Final Office Action dated Nov. 16, 2015", 13 pgs.
"U.S. Appl. No. 12/938,202, Response filed Mar. 3, 2014 to Final Office Action dated Jan. 16, 2014", 4 pgs.
"U.S. Appl. No. 12/938,202, Response filed Apr. 18, 2013 to Restriction Requirement dated Mar. 20, 2013", 9 pgs.
"U.S. Appl. No. 12/938,202, Response filed May 26, 2015 to Final Office Action dated Feb. 27, 2015", 12 pgs.
"U.S. Appl. No. 12/938,202, Response filed Jul. 27, 2015 to Advisory Action dated Jun. 30, 2015", 13 pgs.
"U.S. Appl. No. 12/938,202, Response filed Sep. 18, 2013 to Non Final Office Action dated Jun. 26, 2013", 17 pgs.
"U.S. Appl. No. 12/938,202, Response filed Nov. 3, 2014 to Non Final Office Action dated Sep. 10, 2014", 17 pgs.
"U.S. Appl. No. 12/938,202, Restriction Requirement dated Mar. 20, 2013", 6 pgs.
Barker, John Michael, et al., "Temporary Neurostimulation Lead Identification Device", U.S. Appl. No. 61/030,506, filed Feb. 21, 2008.

\* cited by examiner

CHARGE RECOVERY BI-PHASIC CONTROL FOR TISSUE STIMULATION

RELATED APPLICATION

The present application is a continuation of U.S. patent application Ser. No. 12/938,202, filed Nov. 2, 2010, now issued as U.S. Pat. No. 9,415,223, which claims the benefit under 35 U.S.C. § 119 to U.S. provisional patent application Ser. No. 61/257,279, filed Nov. 2, 2009. The foregoing is applications are hereby incorporated by reference into the present application in their entirety.

FIELD OF THE INVENTION

The present invention relates to tissue stimulation systems, and more particularly, to a system and method for electrically stimulating tissue.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, in recent investigations Peripheral Nerve Stimulation (PNS) systems have demonstrated efficacy in the treatment of chronic pain syndromes and incontinence, and a number of additional applications are currently under investigation. Furthermore, Functional Electrical Stimulation (FES) systems such as the Freehand system by NeuroControl (Cleveland, Ohio) have been applied to restore some functionality to paralyzed extremities in spinal cord injury patients.

Each of these implantable neurostimulation systems typically includes an electrode lead implanted at the desired stimulation site and an implantable pulse generator (IPG) implanted remotely from the stimulation site, but coupled either directly to the electrode lead or indirectly to the electrode lead via a lead extension. Thus, electrical pulses can be delivered from the neurostimulator to the stimulation electrode(s) to stimulate or activate a volume of tissue in accordance with a set of stimulation parameters and provide the desired efficacious therapy to the patient. A typical stimulation parameter set may include the electrodes that are sourcing (anodes) or returning (cathodes) the stimulation current at any given time, as well as the amplitude, duration, rate, and burst rate of the stimulation pulses.

The neurostimulation system may further comprise a handheld remote control (RC) to remotely instruct the neurostimulator to generate electrical stimulation pulses in accordance with selected stimulation parameters. The RC may, itself, be programmed by a technician attending the patient, for example, by using a Clinician's Programmer (CP), which typically includes a general purpose computer, such as a laptop, with a programming software package installed thereon. If the IPG contains a rechargeable battery, the neurostimulation system may further comprise an external charger capable of transcutaneously recharging the IPG via inductive energy.

The stimulation energy may be delivered between electrodes as monophasic electrical energy or multiphasic electrical energy. Monophasic electrical energy includes a series of pulses that are either all positive (anodic) or all negative (cathodic). Multiphasic electrical energy includes a series of pulses that alternate between positive and negative. For example, multiphasic electrical energy may include a series of biphasic pulses, with each biphasic pulse including a cathodic (negative) stimulation phase and an anodic (positive) charge recovery phase that is generated after the stimulation phase to prevent direct current charge transfer through the tissue, thereby avoiding cell trauma and electrode degradation via corrosion. That is, charge is conveyed through the electrode-tissue interface via current at an electrode during a stimulation period (the length of the stimulation pulse), and then pulled back off the electrode-tissue interface via an oppositely polarized current at the same electrode during a recharge period (the length of the recharge pulse).

In prior art systems, the charge recovery phase is not intended to provide a therapeutic effect, and is solely used to recover the charge created by the stimulation phase. This charge recovery phase requires additional electrical energy that may otherwise be used as stimulation energy to provide the therapeutic effect to the patient. Because battery power for an IPG is a limited resource that must be periodically replenished via use of the external recharger, or in cases where the battery is not rechargeable, can only be replaced after surgically explanting the IPG, it is desirable to conserve as much battery power in the IPG as possible.

There, thus, remains a need for an improved method and system that utilizes bi-phasic electrical energy is a more efficient manner to provide stimulation therapy to tissue.

SUMMARY OF THE INVENTION

In accordance with a first aspect of the present inventions, a method of providing therapy to a patient using first and second electrodes implanted within the patient is provided. The method comprises generating a train of electrical multi-phasic pulses. If each multi-phasic pulse is a bi-phasic pulse, it may be symmetrical or asymmetrical. The method further comprises sourcing a first electrical current from the second electrode and sinking at least a portion of the first electrical current to the first electrode during a stimulation phase of each multi-phasic pulse, thereby therapeutically stimulating a first tissue region adjacent the first electrode. The method further comprises sourcing a second electrical current from the first electrode and sinking at least a portion of the second electrical current to the second electrode during a charge recovery phase of each multi-phasic pulse, thereby recovering at least a portion of the charge that had been injected into the patient during the stimulation phase of each multi-phasic pulse, and therapeutically stimulating a second tissue region adjacent the second electrode. In one method, the first and second tissue regions are contiguous with each other.

In one method, the first electrical current sourced from the second electrode during the stimulation phase of each multi-phasic pulse does not stimulate the second tissue region, and the second electrical current sourced from the first electrode during the charge recovery phase of each multi-phasic pulse does not stimulate the first tissue region. In another method, no electrical current is conveyed between the first electrode and the second electrode during an interphase between the stimulation phase and the charge recovery phase of each multi-phasic pulse. Interphase may be at least one-half of the stimulation phase, so that the phases of each multi-phasic pulse do not interfere with each other.

Still another method further comprises sinking another portion of the first electrical current to a third electrode implanted within the patient during the stimulation phase of each multi-phasic pulse, wherein a third tissue region adjacent the third electrode is not stimulated, and sourcing a third electrical current from the third electrode and sinking at least a portion of the third electrical current to the second electrode during the charge recovery phase of each multi-phasic pulse, thereby, in combination with the at least a portion of the second electrical current sunk to the second electrode, recovering the at least a portion of the charge injected into the patient during the stimulation phase of each multi-phasic pulse, and therapeutically stimulating the second tissue region adjacent the second electrode.

In another method, the first electrode has a first stimulation threshold during the stimulation phase of each multi-phasic pulse, and the second electrode has a second stimulation threshold different from the first stimulation threshold during the charge recovery phase of each multi-phasic pulse. In this case, the electrical current may be conveyed between the first and second electrodes during the stimulation and charge recovery phases of each multi-phasic pulse in a manner that prevents excessive stimulation of the first and second target tissue regions.

For example, the method may further comprise performing at least one of the following steps: sinking another portion of the first electrical current to a third electrode implanted within the patient during the stimulation phase of each multi-phasic pulse if the first stimulation threshold is less than the second stimulation threshold, and sinking another portion of the second electrical current to a third electrode implanted within the patient during the charge recovery phase of each multi-phasic pulse if the second stimulation threshold is less than the first stimulation threshold.

As another example, the method may further comprise performing at least one of the following steps: adjusting the duration of the stimulation phase to be longer than the duration of the charge recovery phase of each multi-phasic pulse if the first stimulation threshold is less than the second stimulation threshold, and adjusting the duration of the charge recovery phase to be longer than the duration of the stimulation phase of each multi-phasic pulse if the second stimulation threshold is less than the first stimulation threshold.

In accordance with a second aspect of the present inventions, an external control device for controlling a neurostimulator and associated first and second electrodes implanted within a patient is provided. The external control device comprises a user interface configured for receiving an input from a user that defines the first and second electrodes as tissue stimulating electrodes, and telemetry circuitry configured for wirelessly communicating with the neurostimulator. The external control device further comprises a processor configured for generating and transmitting instructions to the neurostimulator via the telemetry circuitry to generate a train of electrical multi-phasic pulses, source a first electrical current from the second electrode and sink at least a portion of the first electrical current to the first electrode during a stimulation phase of each multi-phasic pulse in a manner that would therapeutically stimulate a first tissue region adjacent the first electrode, and to source a second electrical current from the first electrode and sink at least a portion of the second electrical current to the second electrode during a charge recovery phase of each multi-phasic pulse in a manner that recovers at least a portion of the charge that had been injected into the patient during the stimulation phase of each multi-phasic pulse, and therapeutically stimulates a second tissue region adjacent the second electrode.

In one embodiment, the processor is configured for generating and transmitting instructions to the neurostimulator via the telemetry circuitry to source the first electrical current from the second electrode during the stimulation phase of each multi-phasic pulse in a manner that does not stimulate the second tissue region, and source the second electrical current from the first electrode during the charge recovery phase of each multi-phasic pulse in a manner that does not stimulate the first tissue region. In another embodiment, the processor is configured for generating and transmitting instructions to the neurostimulator via the telemetry circuitry to adjust an interphase between the stimulation phase and the charge recovery phase of each multi-phasic pulse. The interphase may be at least one-half of the stimulation phase to ensure that both phases of the multi-phasic pulse do not interfere with each other.

In another embodiment, the processor is configured for generating and transmitting instructions to the neurostimulator via the telemetry circuitry to sink another portion of the first electrical current to a third electrode implanted within the patient during the stimulation phase of each multi-phasic pulse in a manner that does not stimulate a third tissue region adjacent the third electrode, and to source a third electrical current from the third electrode and sink at least a portion of the third electrical current to the second electrode during the charge recovery phase of each multi-phasic pulse in a manner that, in combination with the at least a portion of the second electrical current sunk to the second electrode, recovers the at least a portion of the charge injected into the patient during the stimulation phase of each multi-phasic pulse, and therapeutically stimulates the second tissue region adjacent the second electrode.

In still another embodiment, the processor is configured for generating and transmitting instructions to the neurostimulator via the telemetry circuitry to sink a first test electrical current to the first electrode from the first tissue region, and to sink a second test electrical current to the second electrode from the second tissue region, determine a first stimulation threshold of the first electrode based on the first test electrical current, and determine a second stimulation threshold of the second electrode based on the second test electrical current. In this case, the processor may be configured for generating and transmitting instructions to the neurostimulator via the telemetry circuitry based on the determined first and second stimulation thresholds to convey electrical current between the first and second electrodes during the stimulation and charge recovery phases of each multi-phasic pulse in a manner that prevents excessive stimulation of the first and second target tissue regions.

For example, the processor may be configured for generating and transmitting instructions to the neurostimulator via the telemetry circuitry to perform at least one of the following steps: sink another portion of the first electrical current to a third electrode implanted within the patient during the stimulation phase of each multi-phasic pulse if the first stimulation threshold is less than the second stimulation threshold, and sink another portion of the second electrical current to the third electrode during the charge recovery phase of each multi-phasic pulse if the second stimulation threshold is less than the first stimulation threshold.

As another example, the processor may be configured for generating and transmitting instructions to the neurostimulator via the telemetry circuitry to perform at least one of the following steps: adjust the duration of the stimulation phase of each multi-phasic pulse to be longer than the duration of the charge recovery phase of each multi-phasic pulse if the first stimulation threshold is less than the second stimulation threshold, and adjust the duration of the charge recovery phase of each multi-phasic pulse to be longer than the duration of the stimulation phase of each multi-phasic pulse if the second stimulation threshold is less than the first stimulation threshold.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

The description that follows relates to a spinal cord stimulation (SCS) system. However, it is to be understood that while the invention lends itself well to applications in SCS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

Figure 1:
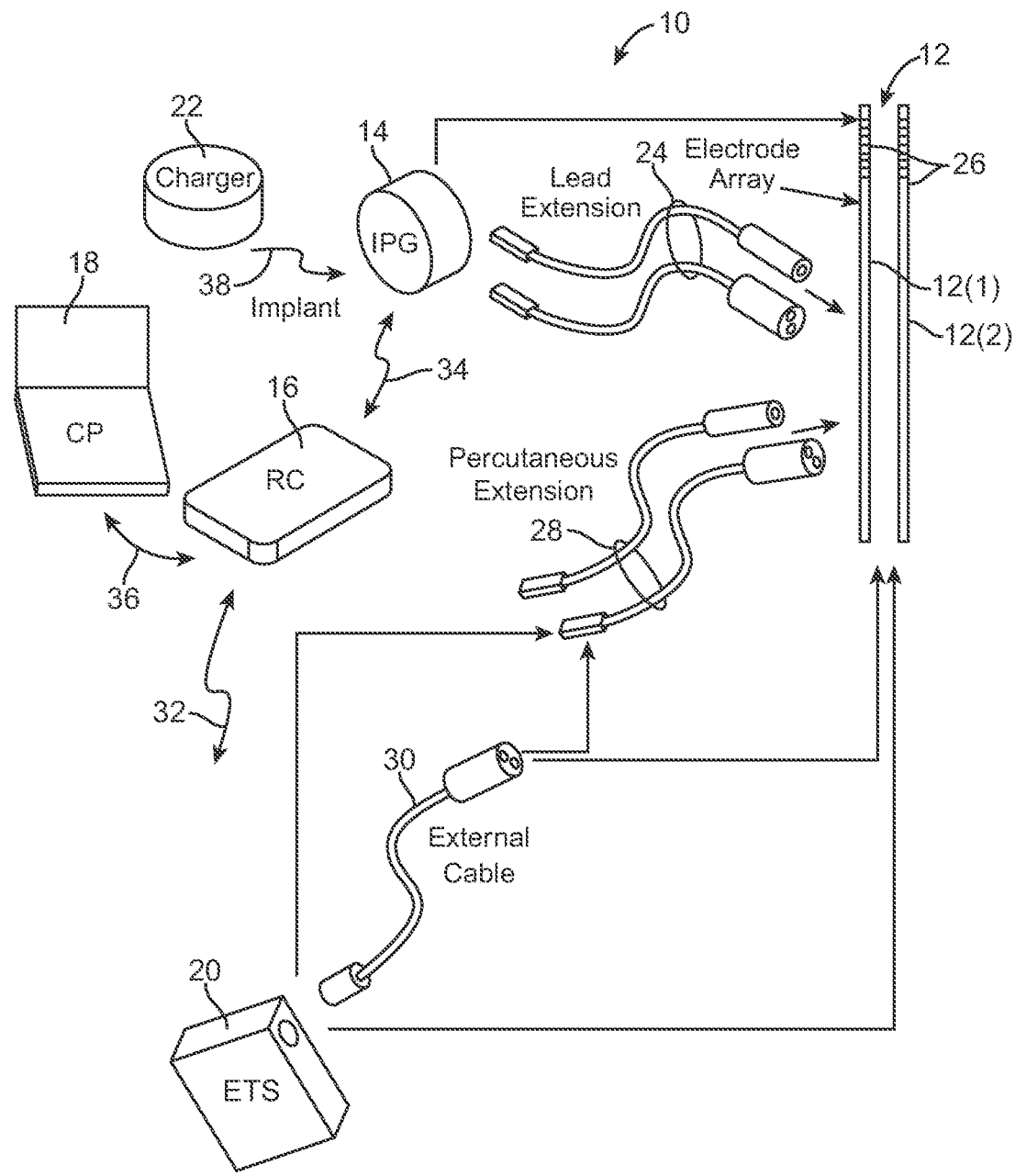
FIG. 1 is plan view of one embodiment of a spinal cord stimulation (SCS) system arranged in accordance with the present inventions.

Turning first to FIG. 1, an exemplary SCS system 10 generally comprises a plurality of percutaneous leads 12 (in this case, two percutaneous leads 12(1) and 12(2)), an implantable pulse generator (IPG) 14, an external remote control (RC) 16, a Clinician's Programmer (CP) 18, an External Trial Stimulator (ETS) 20, and an external charger 22.

The IPG 14 is physically connected via two lead extensions 24 to the stimulation leads 12, which carry a plurality of electrodes 26 arranged in an array. As will also be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters. The IPG 14 and stimulation leads 12 can be provided as an implantable neurostimulation kit, along with, e.g., a hollow needle, a stylet, a tunneling tool, and a tunneling straw. Further details discussing implantable kits are disclosed in U.S. Application Ser. No. 61/030,506, entitled "Temporary Neurostimulation Lead Identification Device," which is expressly incorporated herein by reference.

The ETS 20 may also be physically connected via percutaneous lead extensions 28 or external cable 30 to the stimulation lead 12. The ETS 20, which has similar pulse generation circuitry as the IPG 14, also delivers electrical stimulation energy in the form of a pulse electrical waveform to the electrode array 26 in accordance with a set of stimulation parameters. The major difference between the ETS 20 and the IPG 14 is that the ETS 20 is a non-implantable device that is used on a trial basis after the stimulation lead 12 has been implanted and prior to implantation of the IPG 14, to test the responsiveness of the stimulation that is to be provided. Further details of an exemplary ETS are described in U.S. Pat. No. 6,895,280, which is expressly incorporated herein by reference.

The RC 16 may be used to telemetrically control the ETS 20 via a bi-directional RF communications link 32. Once the IPG 14 and stimulation lead 12 is implanted, the RC 16 may be used to telemetrically control the IPG 14 via a bi-directional RF communications link 34. Such control allows the IPG 14 to be turned on or off and to be programmed with different stimulation programs after implantation. Once the IPG 14 has been programmed, and its power source has been charged or otherwise replenished, the IPG 14 may function as programmed without the RC 16 being present.

The CP 18 provides clinician detailed stimulation parameters for programming the IPG 14 and ETS 20 in the operating room and in follow-up sessions. The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown).

The external charger 22 is a portable device used to transcutaneously charge the IPG 14 via an inductive link 38. For purposes of brevity, the details of the external charger 22 will not be described herein. Details of exemplary embodiments of external chargers are disclosed in U.S. Pat. No. 6,895,280, which has been previously incorporated herein by reference. Once the IPG 14 has been programmed, and its power source has been charged by the external charger 22 or otherwise replenished, the IPG 14 may function as programmed without the RC 16 or CP 18 being present.

Figure 2:
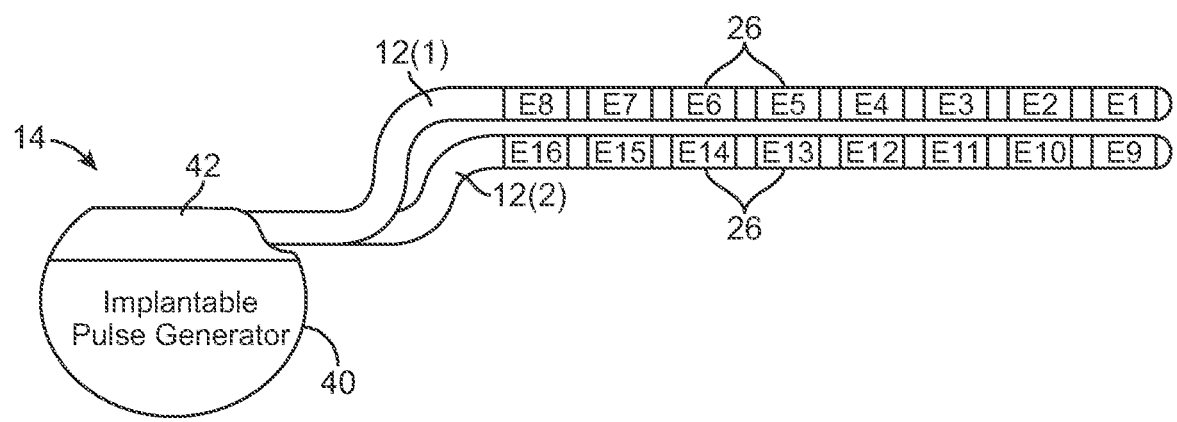
FIG. 2 is a plan view of an implantable pulse generator (IPG) and another embodiment of a percutaneous stimulation lead used in the SCS system of FIG. 1.

Referring now to FIG. 2, the external features of the stimulation leads 12 and the IPG 14 will be briefly described. Each of the stimulation leads 12 has eight electrodes 26 (respectively labeled E1-E8 and E9-E16). The actual number and shape of leads and electrodes will, of course, vary according to the intended application. Further details describing the construction and method of manufacturing percutaneous stimulation leads are disclosed in U.S. patent application Ser. No. 11/689,918, entitled "Lead Assembly and Method of Making Same," and U.S. patent application Ser. No. 11/565,547, entitled "Cylindrical Multi-Contact Electrode Lead for Neural Stimulation and Method of Making Same," the disclosures of which are expressly incorporated herein by reference.

The IPG 14 comprises an outer case 40 for housing the electronic and other components (described in further detail below). The outer case 40 is composed of an electrically conductive, biocompatible material, such as titanium, and forms a hermetically sealed compartment wherein the internal electronics are protected from the body tissue and fluids. In some cases, the outer case 40 may serve as an electrode. The IPG 14 further comprises a connector 42 to which the proximal ends of the stimulation leads 12 mate in a manner that electrically couples the electrodes 26 to the internal electronics (described in further detail below) within the outer case 40. To this end, the connector 42 includes two ports (not shown) for receiving the proximal ends of the three percutaneous leads 12. In the case where the lead extensions 24 are used, the ports may instead receive the proximal ends of such lead extensions 24.

As will be described in further detail below, the IPG 14 includes pulse generation circuitry that provides electrical stimulation energy to the electrodes 26 in accordance with a set of parameters. Such parameters may comprise electrode combinations, which define the electrodes that are activated as anodes (positive), cathodes (negative), and turned off (zero), and electrical pulse parameters, which define the pulse amplitude (measured in milliamps or volts depending on whether the IPG 14 supplies constant current or constant voltage to the electrodes), pulse duration (measured in microseconds), pulse rate (measured in pulses per second), and pulse shape.

With respect to the pulse patterns provided during operation of the SCS system 10, electrodes that are selected to transmit or receive electrical energy are referred to herein as "activated," while electrodes that are not selected to transmit or receive electrical energy are referred to herein as "non-activated." Electrical energy delivery will occur between two (or more) electrodes, one of which may be the IPG case 40, so that the electrical current has a path from the energy source contained within the IPG case 40 to the tissue and a sink path from the tissue to the energy source contained within the case. Electrical energy may be transmitted to the tissue in a monopolar or multipolar (e.g., bipolar, tripolar, etc.) fashion.

Monopolar delivery occurs when a selected one or more of the lead electrodes 26 is activated along with the case 40 of the IPG 14, so that electrical energy is transmitted between the selected electrode 26 and case 40. Monopolar delivery may also occur when one or more of the lead electrodes 26 are activated along with a large group of lead electrodes located remotely from the one or more lead electrodes 26 so as to create a monopolar effect; that is, electrical energy is conveyed from the one or more lead electrodes 26 in a relatively isotropic manner. Bipolar delivery occurs when two of the lead electrodes 26 are activated as anode and cathode, so that electrical energy is transmitted between the selected electrodes 26. Tripolar delivery occurs when three of the lead electrodes 26 are activated, two as anodes and the remaining one as a cathode, or two as cathodes and the remaining one as an anode.

Significantly, the stimulation energy is delivered between the electrodes 26 as multiphasic electrical energy, and in particular, biphasic electrical energy. Like in the prior art, the train of electrical bi-phasic pulses is designed to prevent direct current charge transfer through the tissue, thereby avoiding electrode degradation and cell trauma. However, unlike with the prior art, both phases of each electrical bi-phasic pulses are designed to stimulate tissue, thereby providing a more efficient use of the battery power. The details of the technique for using both phases of bi-phasic pulses to stimulate tissue will be described below.

Figure 3:
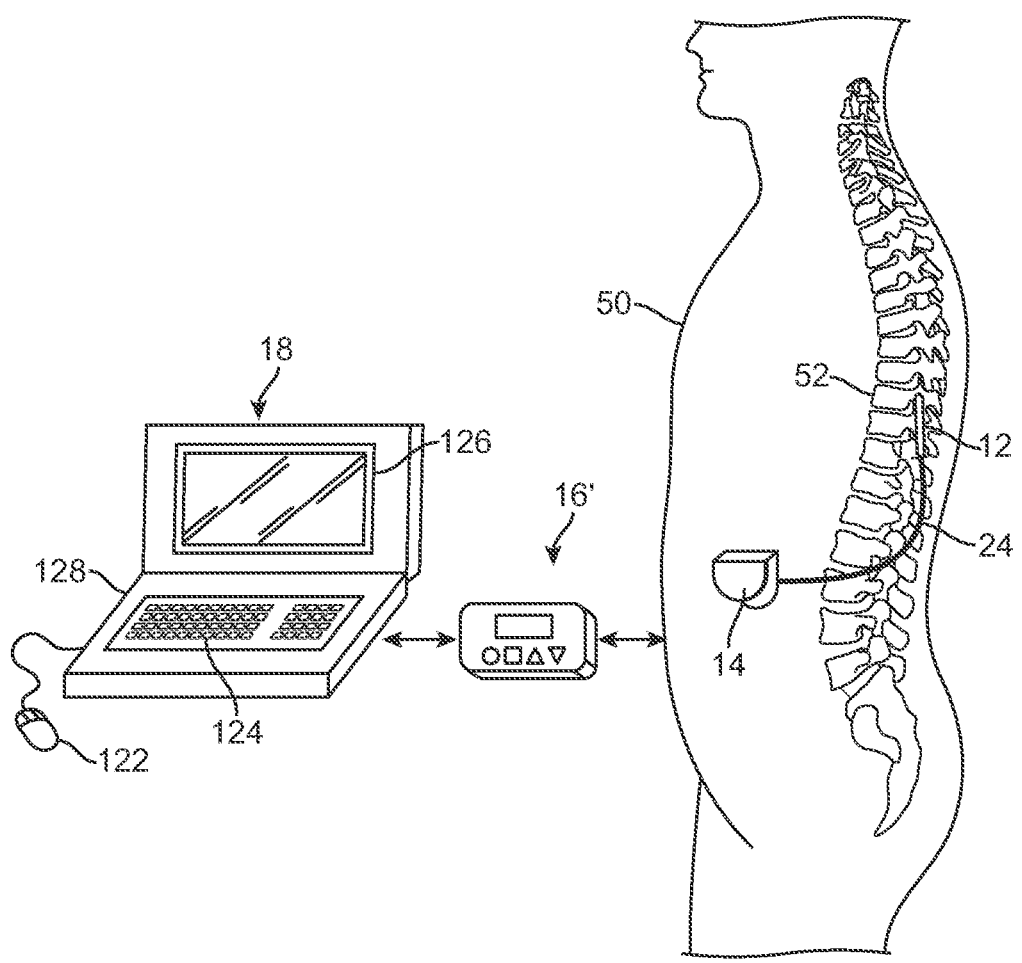
FIG. 3 is a plan view of the SCS system of FIG. 1 in use with a patient.

Referring to FIG. 3, the stimulation leads 12 are implanted within the spinal column 46 of a patient 48. The preferred placement of the stimulation leads 12 is adjacent, i.e., resting near, or upon the dura, adjacent to the spinal cord area to be stimulated. Due to the lack of space near the location where the stimulation leads 12 exit the spinal column 46, the IPG 14 is generally implanted in a surgically-made pocket either in the abdomen or above the buttocks. The IPG 14 may, of course, also be implanted in other locations of the patient's body. The lead extensions 24 facilitate locating the IPG 14 away from the exit point of the stimulation leads 12. As there shown, the CP 18 communicates with the IPG 14 via the RC 16. While the stimulation leads 12 are illustrated as being implanted near the spinal cord area of a patient, the stimulation leads 12 may be implanted anywhere in the patient's body, including a peripheral region, such as a limb, or the brain. After implantation, the IPG 14 is used to provide the therapeutic stimulation under control of the patient.

Figure 4:
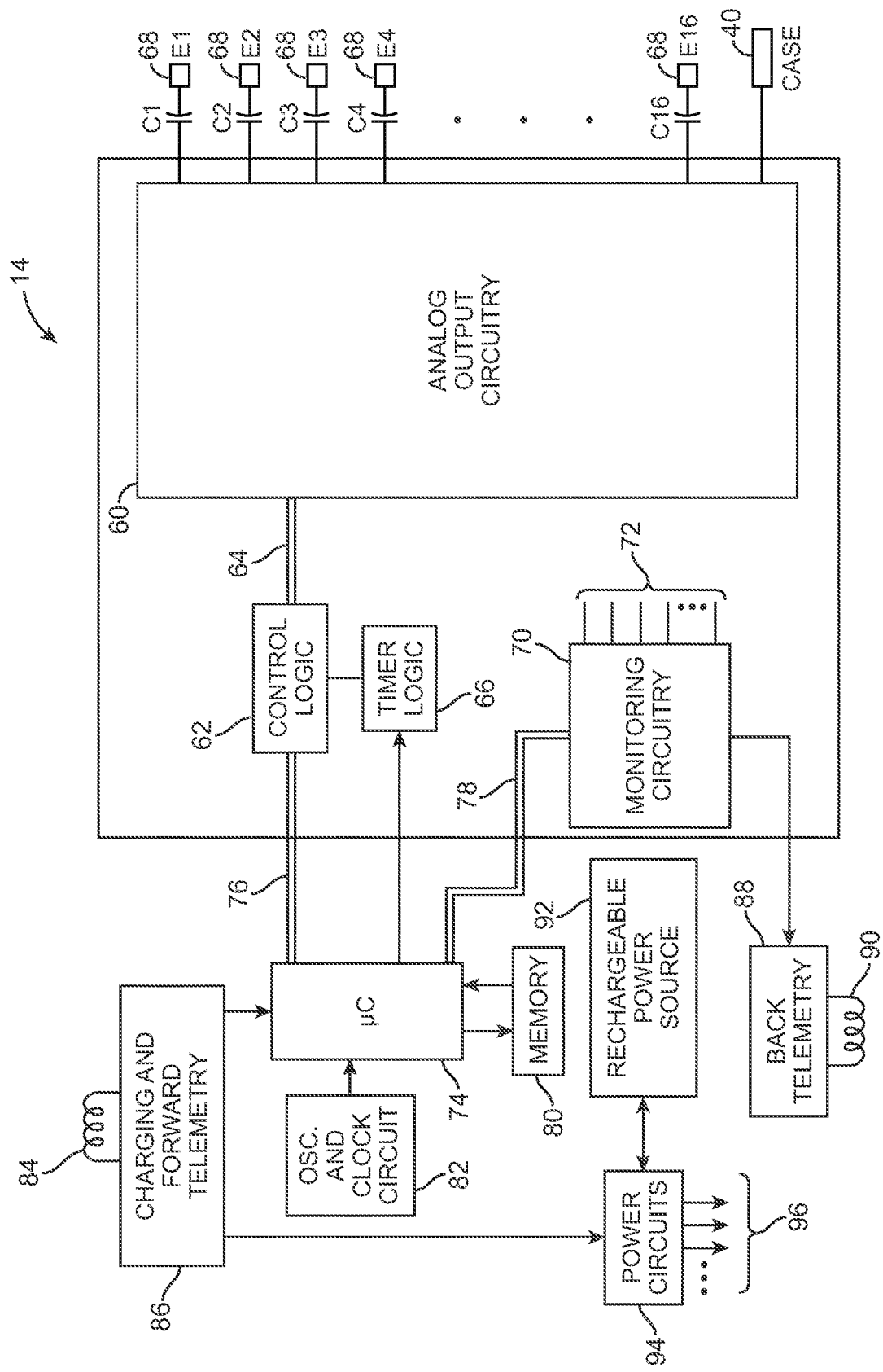
FIG. 4 is a block diagram of the internal components of the IPG of FIG. 1.

Turning next to FIG. 4, the main internal components of the IPG 14 will now be described. The IPG 14 includes stimulation output circuitry 60 configured for generating electrical stimulation energy in accordance with a defined pulsed waveform having a specified pulse amplitude, pulse rate, pulse width, pulse shape, and burst rate under control of control logic 62 over data bus 64. Control of the pulse rate and pulse width of the electrical waveform is facilitated by timer logic circuitry 66, which may have a suitable resolution, e.g., 10 μs. The stimulation energy generated by the stimulation output circuitry 60 is output via capacitors C1-C16 to electrical terminals 68 corresponding to the electrodes 26.

The analog output circuitry 60 may either comprise independently controlled current sources for providing stimulation pulses of a specified and known amperage to or from the electrical terminals 68, or independently controlled voltage sources for providing stimulation pulses of a specified and known voltage at the electrical terminals 68 or to multiplexed current or voltage sources that are then connected to the electrical terminals 68. The operation of this analog output circuitry, including alternative embodiments of suitable output circuitry for performing the same function of generating stimulation pulses of a prescribed amplitude and width, is described more fully in U.S. Pat. Nos. 6,516,227 and 6,993,384, which are expressly incorporated herein by reference.

The IPG 14 further comprises monitoring circuitry 70 for monitoring the status of various nodes or other points 72 throughout the IPG 14, e.g., power supply voltages, temperature, battery voltage, and the like. Notably, the electrodes 26 fit snugly within the epidural space of the spinal column, and because the tissue is conductive, electrical measurements can be taken from the electrodes 26. The IPG 14 further comprises processing circuitry in the form of a microcontroller 74 that controls the control logic 62 over data bus 76, and obtains status data from the monitoring circuitry 70 via data bus 78. The microcontroller 74 additionally controls the timer logic 66. The IPG 14 further comprises memory 80 and an oscillator and clock circuit 82 coupled to the microcontroller 74. The microcontroller 74, in combination with the memory 80 and oscillator and clock circuit 82, thus comprise a microprocessor system that carries out a program function in accordance with a suitable program stored in the memory 80. Alternatively, for some applications, the function provided by the microprocessor system may be carried out by a suitable state machine.

Thus, the microcontroller 74 generates the necessary control and status signals, which allow the microcontroller 74 to control the operation of the IPG 14 in accordance with a selected operating program and parameters. In controlling the operation of the IPG 14, the microcontroller 74 is able to individually generate electrical pulses at the electrodes 26 using the analog output circuitry 60, in combination with the control logic 62 and timer logic 66, thereby allowing each electrode 26 to be paired or grouped with other electrodes 26, including the monopolar case electrode, and to control the polarity, amplitude, rate, and pulse width through which the current stimulus pulses are provided.

The IPG 14 further comprises an alternating current (AC) receiving coil 84 for receiving programming data (e.g., the operating program and/or stimulation parameters) from the RC 16 in an appropriate modulated carrier signal, and charging and forward telemetry circuitry 86 for demodulating the carrier signal it receives through the AC receiving coil 84 to recover the programming data, which programming data is then stored within the memory 80, or within other memory elements (not shown) distributed throughout the IPG 14.

The IPG 14 further comprises back telemetry circuitry 88 and an alternating current (AC) transmission coil 90 for sending informational data (including the field potential and impedance data) sensed through the monitoring circuitry 70 to the RC 16. The back telemetry features of the IPG 14 also allow its status to be checked. For example, any changes made to the stimulation parameters are confirmed through back telemetry, thereby assuring that such changes have been correctly received and implemented within the IPG 14. Moreover, upon interrogation by the RC 16, all programmable settings stored within the IPG 14 may be uploaded to the RC 16.

The IPG 14 further comprises a rechargeable power source 92 and power circuits 94 for providing the operating power to the IPG 14. The rechargeable power source 92 may, e.g., comprise a lithium-ion or lithium-ion polymer battery. The rechargeable battery 92 provides an unregulated voltage to the power circuits 94. The power circuits 94, in turn, generate the various voltages 96, some of which are regulated and some of which are not, as needed by the various circuits located within the IPG 14. The rechargeable power source 92 is recharged using rectified AC power (or DC power converted from AC power through other means, e.g., efficient AC-to-DC converter circuits) received by the AC receiving coil 84. To recharge the power source 92, an external charger (not shown), which generates the AC magnetic field, is placed against, or otherwise adjacent, to the patient's skin over the implanted IPG 14. The AC magnetic field emitted by the external charger induces AC currents in the AC receiving coil 84. The charging and forward telemetry circuitry 86 rectifies the AC current to produce DC current, which is used to charge the power source 92. While the AC receiving coil 84 is described as being used for both wirelessly receiving communications (e.g., programming and control data) and charging energy from the external device, it should be appreciated that the AC receiving coil 84 can be arranged as a dedicated charging coil, while another coil, such as coil 90, can be used for bi-directional telemetry.

It should be noted that the diagram of FIG. 4 is functional only, and is not intended to be limiting. Those of skill in the art, given the descriptions presented herein, should be able to readily fashion numerous types of IPG circuits, or equivalent circuits, that carry out the functions indicated and described. It should be noted that rather than an IPG for the neurostimulator, the SCS system 10 may alternatively utilize an implantable receiver-stimulator (not shown) connected to the stimulation leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation in accordance with the control signals.

Figure 5:
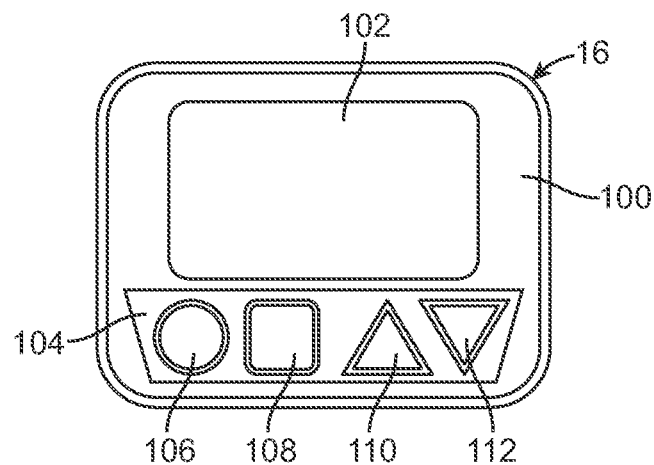
FIG. 5 is a plan view of a remote control that can be used in the SCS system of FIG. 1.

Referring now to FIG. 5, one exemplary embodiment of an RC 16 will now be described. As previously discussed, the RC 16 is capable of communicating with the IPG 14, CP 18, or ETS 20. The RC 16 comprises a casing 100, which houses internal componentry (including a printed circuit board (PCB)), and a lighted display screen 102 and button pad 104 carried by the exterior of the casing 100. In the illustrated embodiment, the display screen 102 is a lighted flat panel display screen, and the button pad 104 comprises a membrane switch with metal domes positioned over a flex circuit, and a keypad connector connected directly to a PCB. In an optional embodiment, the display screen 102 has touchscreen capabilities. The button pad 104 includes a multitude of buttons 106, 108, 110, and 112, which allow the IPG 14 to be turned ON and OFF, provide for the adjustment or setting of stimulation parameters within the IPG 14, and provide for selection between screens.

In the illustrated embodiment, the button 106 serves as an ON/OFF button that can be actuated to turn the IPG 14 ON and OFF. The button 108 serves as a select button that allows the RC 106 to switch between screen displays and/or parameters. The buttons 110 and 112 serve as up/down buttons that can be actuated to increase or decrease any of stimulation parameters of the pulse generated by the IPG 14, including pulse amplitude, pulse width, and pulse rate.

Figure 6:
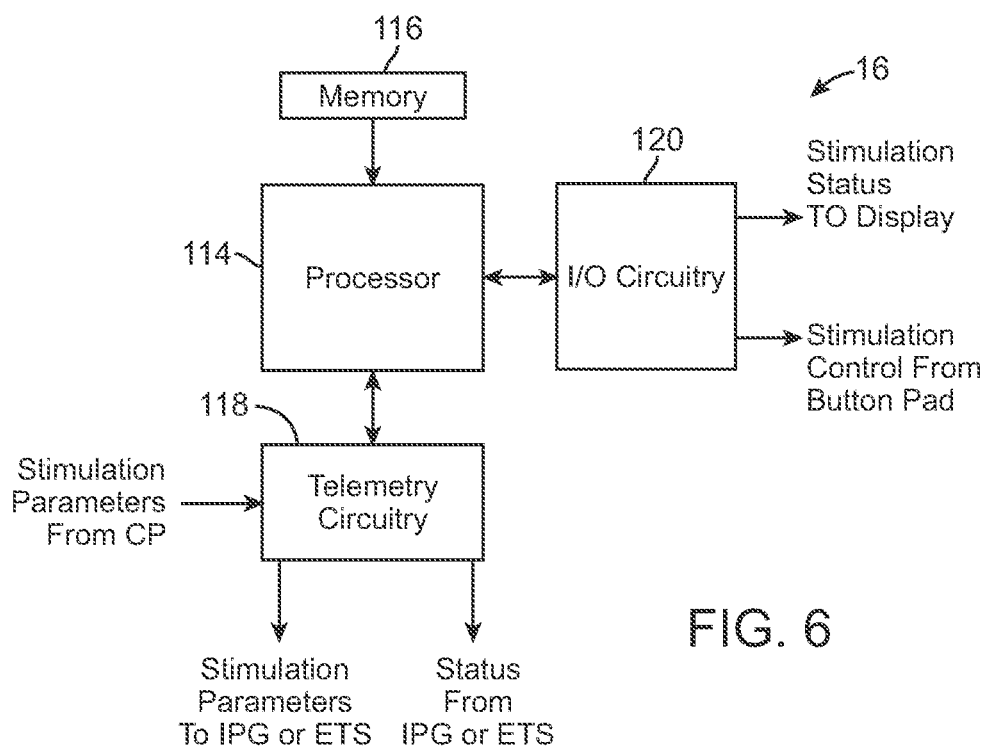
FIG. 6 is a block diagram of the internal componentry of the remote control of FIG. 5.

Referring to FIG. 6, the internal components of an exemplary RC 16 will now be described. The RC 16 generally includes a processor 114 (e.g., a microcontroller), memory 116 that stores an operating program for execution by the processor 114, and telemetry circuitry 118 for transmitting control data (including stimulation parameters and requests to provide status information) to the IPG 14 (or ETS 20) and receiving status information (including the measured electrical data) from the IPG 14 (or ETS 20) via link 34 (or link 32) (shown in FIG. 1), as well as receiving the control data from the CP 18 and transmitting the status data to the CP 18 via link 36 (shown in FIG. 1). The RC 16 further includes input/output circuitry 120 for receiving stimulation control signals from the button pad 104 and transmitting status information to the display screen 102 (shown in FIG. 5). Further details of the functionality and internal componentry of the RC 16 are disclosed in U.S. Pat. No. 6,895,280, which has previously been incorporated herein by reference.

As briefly discussed above, the CP 18 greatly simplifies the programming of multiple electrode combinations, allowing the physician or clinician to readily determine the desired stimulation parameters to be programmed into the IPG 14, as well as the RC 16. Thus, modification of the stimulation parameters in the programmable memory of the IPG 14 after implantation is performed by a clinician using the CP 18, which can directly communicate with the IPG 14 or indirectly communicate with the IPG 14 via the RC 16. That is, the CP 18 can be used by the physician or clinician to modify operating parameters of the electrode array 26 near the spinal cord.

As shown in FIG. 3, the overall appearance of the CP 18 is that of a laptop personal computer (PC), and in fact, may be implemented using a PC that has been appropriately configured to include a directional-programming device and programmed to perform the functions described herein. Thus, the programming methodologies can be performed by executing software instructions contained within the CP 18. Alternatively, such programming methodologies can be performed using firmware or hardware. In any event, the CP 18 may actively control the characteristics of the electrical stimulation generated by the IPG 14 (or ETS 20) to allow the optimum stimulation parameters to be determined based on patient feedback and for subsequently programming the IPG 14 (or ETS 20) with the optimum stimulation parameters.

Figure 7:
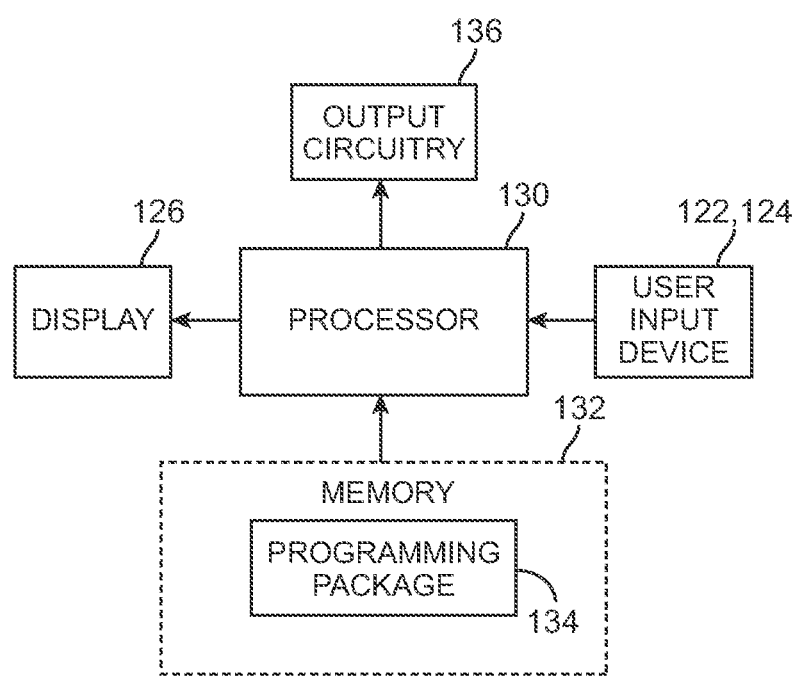
FIG. 7 is a block diagram of the components of a clinician's programmer that can be used in the SCS system of FIG. 1.

To allow the clinician to perform these functions, the CP 18 includes a mouse 121, a keyboard 122, and a programming display screen 124 housed in a case 126. It is to be understood that in addition to, or in lieu of, the mouse 121, other directional programming devices may be used, such as a joystick, or directional keys included as part of the keys associated with the keyboard 122. As shown in FIG. 7, the CP 18 generally includes a processor 128 (e.g., a central processor unit (CPU)) and memory 130 that stores a stimulation programming package 132, which can be executed by the processor 128 to allow a clinician to program the IPG 14 (or ETS 20) and RC 16. The CP 18 further includes telemetry circuitry 134 for downloading stimulation parameters to the RC 16 and uploading stimulation parameters already stored in the memory 116 of the RC 16 via link 36 (shown in FIG. 1). The telemetry circuitry 134 is also configured for transmitting the control data (including stimulation parameters and requests to provide status information) to the IPG 14 (or ETS 20) and receiving status information (including the measured electrical data) from the IPG 14 (or ETS 20) indirectly via the RC 16.

As briefly discussed above, the IPG 14 may deliver stimulation energy in the form of a train of bi-phasic electrical pulses that uses both phases to stimulate tissue. The IPG 14 may accomplish this under control of an external control device, such as the RC 16 and/or CP 18. In particular, a user may define selected ones of the electrodes 16 as active electrodes (both the anodes that source the electrical current and the cathodes that sink the electrical current) in a conventional manner via a user interface of the external control device. For example, the user may operate the user input devices 122, 124 of the CP 18 (shown in FIGS. 3 and 7) to select the active electrodes manually or automatically via current steering, as described in U.S. Provisional Patent Application Ser. No. 61/113,973, entitled "System and Method for Determining Appropriate Steering Tables for Distributing Stimulation Energy Among Multiple Neurostimulation Electrodes," which is expressly incorporated herein by reference.

The external control device can then program the IPG 14 to activate the electrical terminals 68 (and thus the corresponding electrodes 16) that are selected to be activated by the user by generating and transmitting instructions to the IPG 14 via telemetry circuitry (such as circuitry 118 of RC 16 (shown in FIG. 6) or circuitry 136 of CP 18 (shown in FIG. 7)). In response to the user definition of the active electrodes, the external control device may program the IPG 14 in a conventional manner, such that the stimulation of tissue only occurs during the stimulation phase of each bi-phasic pulse, with the charge recovery phase of each bi-phasic pulse only providing the charge recovery function. Significantly, however, the external control device may program the IPG 14 in an unconventional manner, such that stimulation of tissue occurs during both the stimulation phase and the charge recovery phase of each bi-phasic pulse. The external control device can either offer the user the option or autonomously program the IPG 14 in the unconventional manner, such that stimulation occurs during both phases of each bi-phasic pulse.

Figure 8:
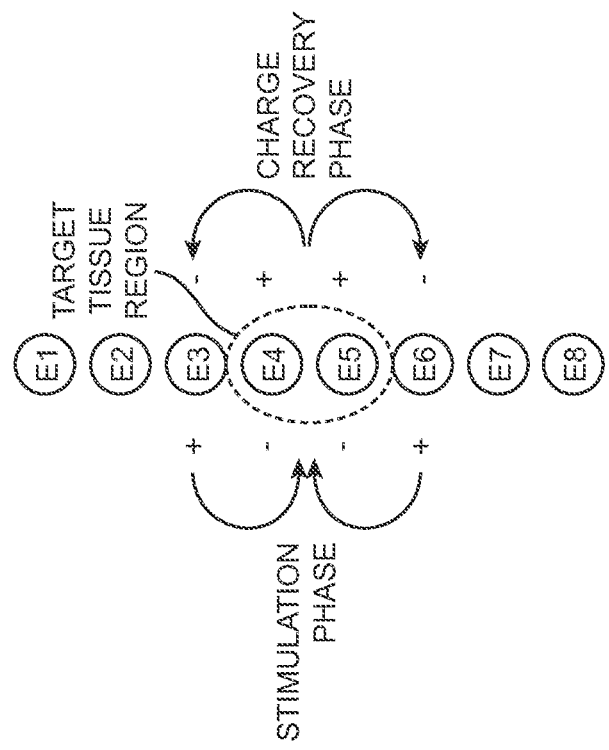
FIG. 8 is a diagram showing the flow of current in an electrode array during a stimulation phase and a charge recovery phase of a conventional bi-phasic pulse.

As an example, and with reference to FIG. 8, assume that it is desirable to stimulate a target tissue region in a patient, and in particular, a target spinal cord tissue region. As shown, electrodes E4 and E5 are located within the target tissue region, whereas electrodes E1-E3 and E6-E8 are located outside the target tissue region. In a conventional technique, the IPG 14 would be programmed to activate electrodes E4 and E5 as cathodes, and any one or more of the electrodes E1-E3 and E6-E8 (e.g., electrodes E2, E6) as anodes for bipolar stimulation or the case 40 of the IPG 14 for monopolar stimulation.

Figure 9A:
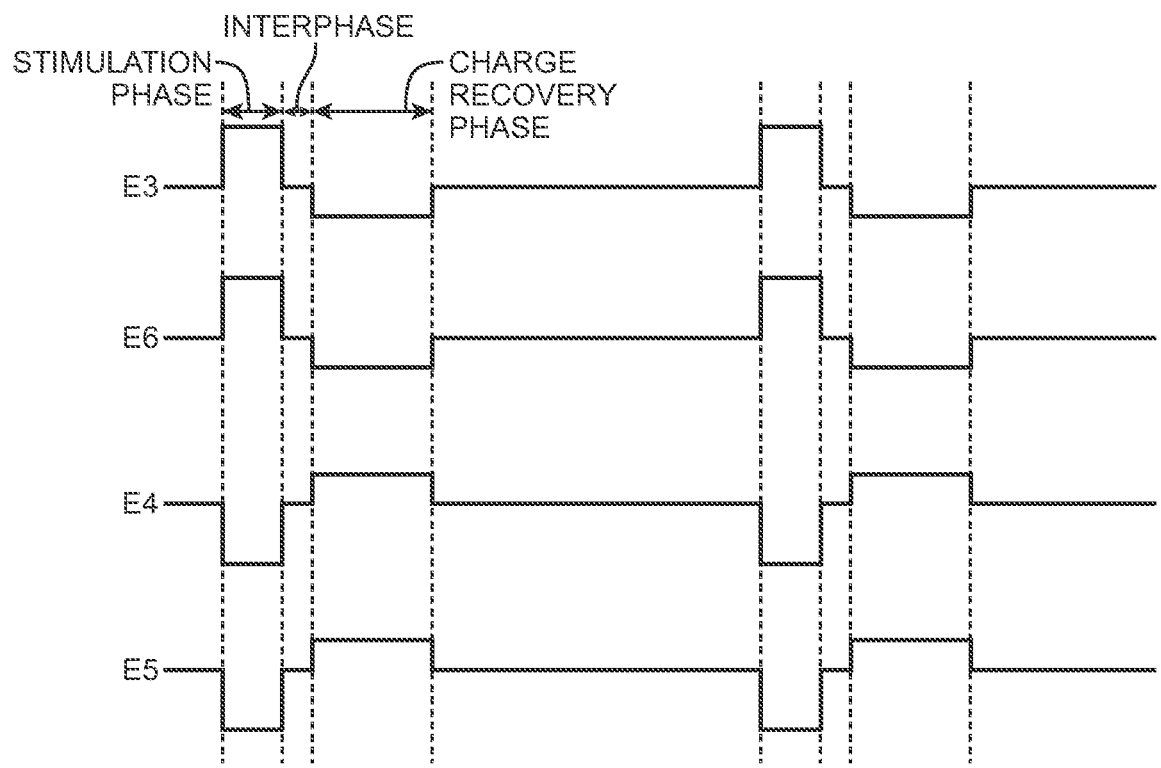
FIGS. 9a and 9b is a timing diagram of one conventional technique that the SCS system of FIG. 1 may use to stimulate tissue using the first phase of a bi-phasic pulse and recover charge from the tissue using the second phase of the bi-phasic pulse.
Figure 9B:
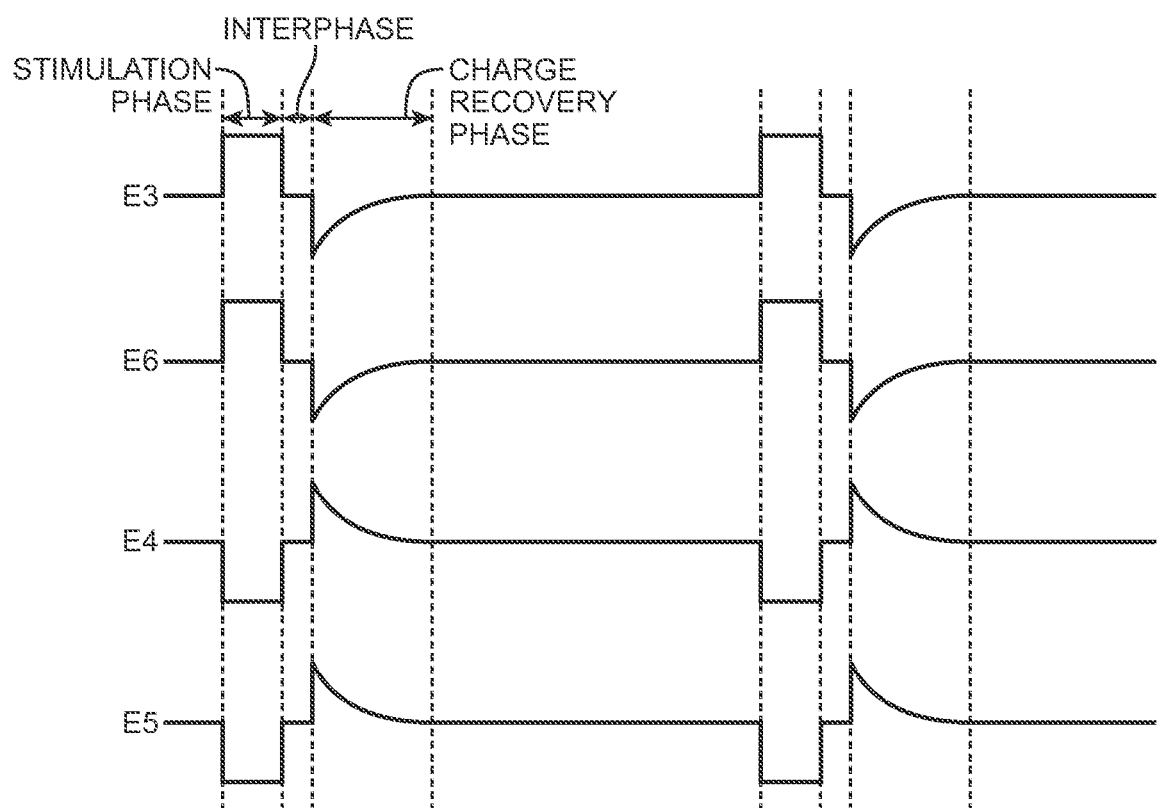

In the conventional case, as shown in FIGS. 9a and 9b, a bi-phasic pulse includes a first phase (stimulation) in which electrical energy of a first polarity is generated, and a second phase (charge recovery) in which electrical energy of a second opposite polarity is generated. As shown in FIG. 9a, the second phase may be an active charge recovery phase, wherein electrical current is actively conveyed through the electrode by turning on the current sources or voltage sources of the analog output circuitry 50 (shown in FIG. 4).

Or, as shown in FIG. 9b, the second phase may be a passive charge recovery phase, wherein electrical current is passively conveyed through the electrode via a recharge or redistribution of the charge flowing from any one or more of the coupling capacitors C1-Cn, while the current sources or voltage sources of the analog output circuitry 50 (shown in FIG. 4) are turned off. Using active charge recovery, as opposed to passive charge recovery, allows faster recharge, while avoiding the charge imbalance that could otherwise occur. In addition to a stimulation phase and a charge recovery phase, each biphasic pulse may include an interphase defining the time period between the stimulation phase and charge recovery phase.

Notably, because the stimulation threshold (i.e., the electrical current needed on an activated electrode to stimulate adjacent tissue) of cathodes is considerably lower (usually, 5 to 20 times) than the stimulation threshold of anodes (i.e., less electrical current is required to flow through a cathode to stimulate adjacent tissue than is required to flow through an anode to stimulate adjacent tissue). Thus, in both cases shown in FIGS. 9a and 9b, the electrical current conveyed during the stimulation phase of each bi-phasic pulse is sourced from selected ones of electrodes E1-E3, E6-E8 (in this case, electrodes E3, E6), and sunk to electrodes E4, E5. Due to the relative stimulation thresholds between cathodes and anodes, the target tissue region adjacent the electrodes E4, E5 (which are cathodic during the stimulation phase) will be stimulated during the stimulation phase of each bi-phasic pulse, whereas the non-target tissue region adjacent the anodic electrodes E3, E6 (which are anodic during the stimulation phase) will not be stimulated during the stimulation phase of each bi-phasic pulse.

In both cases shown in FIGS. 9a and 9b, the electrical current conveyed during the charge recovery phase of each bi-phasic pulse is sourced from electrodes E4, E5, and sunk to electrodes E3, E6. Notably, because the stimulation threshold of tissue relative to anodes is relatively high compared to the stimulation threshold of tissue relative to cathodes, the target tissue region adjacent electrodes E4, E5 (which are anodic during the charge recovery phase) will not be stimulated during the charge recovery phase of each bi-phasic pulse. Furthermore, the recharge pulse is shaped and/or has a magnitude/duration, such that the electrical current sunk into electrodes E3, E6 (which are cathodic during the charge recovery phase) does not stimulate the non-target tissue region.

As briefly discussed above, the use of bi-phasic electrical pulses in this manner is conventional. However, as also discussed briefly above, the second phase of each bi-phasic pulse may be used to not only recover charge in the tissue, but to stimulate the tissue as well. Tissue stimulation during the charge recovery phase can be accomplished by programming the IPG 14 via the external control device to select the first-phase anode or anodes and adjust the second phase electrical current and/or interphase period in a manner that stimulation of the target tissue region adjacent the first-phase anode(s) (i.e., the second-phase cathode(s)) will occur during the charge recovery phase).

For example, the electrical current amplitude during the charge recovery phase of each bi-phasic pulse can be controlled by controlling the duration of the charge recovery phase. In particular, since the actual charge to be recovered is limited by the charge injecting during the phase of the bi-phasic pulse, the injected charge may be recovered more quickly, so that the net cathodic electrical current in the first-phase anode(s) (which are cathode(s) in the charge recovery phase)) during the charge recovery phase is increased, resulting in more likelihood of stimulation of the tissue adjacent the first-phase anode(s)). Ideally, the duration of the charge recovery phase may be in the range of 100-300 microseconds for the most effective stimulation.

As another example, the duration of the interphase between the two phases of each bi-phasic pulse can be controlled. In particular, by adjusting the interphase duration, the relative stimulation threshold between the first phase and the second phase of each bi-phasic pulse can be adjusted due to the non-linear kinetics of the excitable tissue membrane. For example, the duration of the interphase can be set to at least one-half the duration of the first phase to minimize the chance that each phase will affect the stimulation threshold of the other. For example, if the first phase has a duration of 500 microseconds, the duration of the interphase may be at least 250 microseconds.

As still another example, the number of first-phase anodes can be adjusted. In particular, by selecting a lesser number of anodes in the first phase, the concentration of the cathodic current in the first-phase anodes (which are cathode(s) in the charge recovery phase)) during the charge recovery phase is increased, resulting in more likelihood of stimulation of the tissue adjacent the first-phase anode(s). As yet another example, the number of first phase cathodes can be adjusted. In particular, by selecting a greater number of cathodes in the first phase (e.g., by passing sub-threshold electrical current through cathodes not needed to stimulate tissue during the first phase), a greater amount of charge will be injected into the tissue, and thus, a greater amount of charge will need to be removed from the tissue, thereby increasing the net cathodic electrical current in the first-phase anode(s)(which are cathode(s) in the charge recovery phase)) during the charge recovery phase is increased, resulting in more likelihood of stimulation of the tissue adjacent the first-phase anode(s)).

Figure 10:
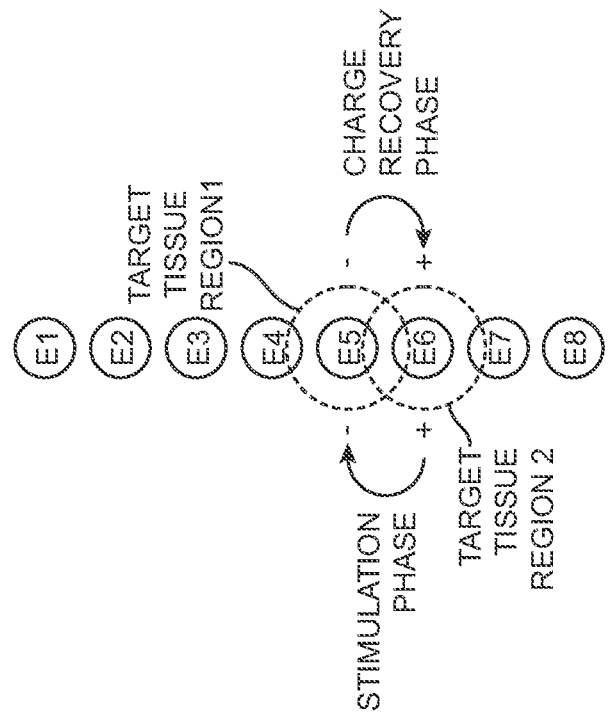
FIG. 10 is a diagram showing the flow of current in an electrode array during a stimulation phase and a charge recovery phase of an unconventional bi-phasic pulse.

In programming the IPG 14, the external control device can use a combination of the foregoing mechanisms to provide stimulation to larger tissue regions and with less total current and power consumption than in the conventional case where cathodic stimulation is only used during the first phase of the bi-phasic pulse. As an example, the IPG 14 may be programmed to activate electrode E4 as a cathode and electrode E5 as an anode during the first phase of each bi-phasic pulse, and activate electrode E4 as an anode and electrode E5 as a cathode during the second phase of each bi-phasic pulse, as shown in FIG. 10.

Figure 11:
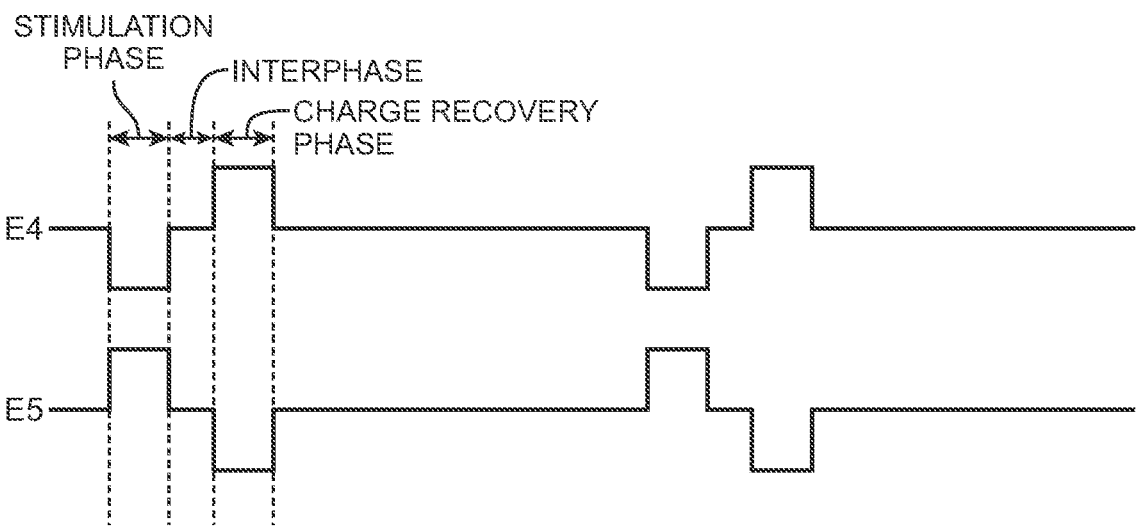
FIG. 11 is a timing diagram of an unconventional technique that the SCS system of FIG. 1 may use to stimulate tissue using the first phase of a bi-phasic pulse and both stimulate tissue and recover charge from the tissue using the second phase of the bi-phasic pulse.

As shown in FIG. 11, a bi-phasic pulse includes a first phase (stimulation) in which electrical energy of a first polarity is generated, and a second phase (stimulation and charge recovery) in which electrical energy of a second opposite polarity is generated. In this case, the bi-phasic-pulses are symmetrical in that the amplitude and shape of the electrical energy conveyed during the first phase is identical to the amplitude and shape of the electrical energy conveyed during the second phase, the difference being that the electrical energy in the respective phases are oppositely polarized.

Notably, because only one first-phase anode is used (i.e., electrode E5) and the amplitude of the charge recovery current is as large as the amplitude of the cathodic electrical current during the first phase (by virtue of the fact that each bi-phasic pulse is symmetrical), stimulation will occur adjacent electrode E5. If, however, more than one first-phase anode is to be used to increase the area of stimulation adjacent the anode(s), the duration of the charge recovery phase can be further decreased to increase the charge recovery current and/or additional cathodes can be used to pass sub-threshold current during the first phase, thereby increasing the charge recover current during the second phase.

Thus, the electrical current conveyed during the first (stimulation) phase of each bi-phasic pulse is sourced from electrode E5 and returned to electrode E4, and the electrical current conveyed during the second phase (charge recovery) of each bi-phasic pulse is sourced from electrode E4 and returned to electrode E5. Again, because the stimulation threshold cathodes are considerably lower than the stimulation threshold of anodes, a first target tissue region adjacent first-phase cathodic E4 will be stimulated during the first phase of each bi-phasic pulse, whereas a second target tissue region adjacent first-phase anodic electrode E5 will not be stimulated during the first phase of each bi-phasic pulse. Likewise, the second target tissue region adjacent second-phase cathodic electrode E5 will be stimulated during the second phase of each bi-phasic pulse, whereas the first target tissue region adjacent second phase anodic electrode E4 will not be stimulated during the second phase of each bi-phasic pulse. In the illustrated embodiment, the target tissue regions adjacent the respective electrodes E4, E5 are contiguous, so that they form a single target tissue region.

Because the electrodes E4, E5 are operated in a bipolar manner during both phases of the bi-phasic pulse, the charge in the tissue resulting from the sourcing of electrical current from electrode E4 as anodic electrical energy during the first phase will balance out the charge in the tissue resulting from the sinking of electrical current to electrode E5 as cathodic electrical energy during the second phase, thereby providing no net DC charge in the target tissue region adjacent electrode E5. Likewise, the charge in the tissue resulting from the sourcing of electrical current from electrode E5 as anodic electrical energy during the second phase will balance out the charge in the tissue resulting from the sinking of electrical current to electrode E4 as cathodic electrical energy during the first phase, thereby providing no net DC charge in the target tissue region adjacent electrode E5.

Notably, in the conventional case where the second phase of each bi-phasic pulse is strictly a charge recovery phase (as shown in FIGS. 9a and 9b), if the stimulation threshold for each activated electrode is 1 mA (i.e., the electrical current needed on each activated electrode to stimulate tissue is 1 mA), the IPG 14 would need to generate and deliver 2 mA of electrical current to stimulate the target tissue region adjacent electrodes E4, E5 during the first phase of each bi-phasic pulse and 2 mA of electrical current to the return electrodes to provide the charge recovery function during the second phase of each bi-phasic pulse. However, in the case where the second phase of each bi-phasic pulse is also used as a stimulation phase (as shown in FIG. 10), if the stimulation threshold for each activated electrode is 1 mA, the IPG 14 would only need to generate and deliver 1 mA of electrical current to stimulate the first target tissue region adjacent electrode E4 during the first phase of each bi-phasic pulse and 1 mA of electrical current to stimulate the second target tissue region adjacent electrode E5 during the second phase of each bi-phasic pulse.

Figure 12:
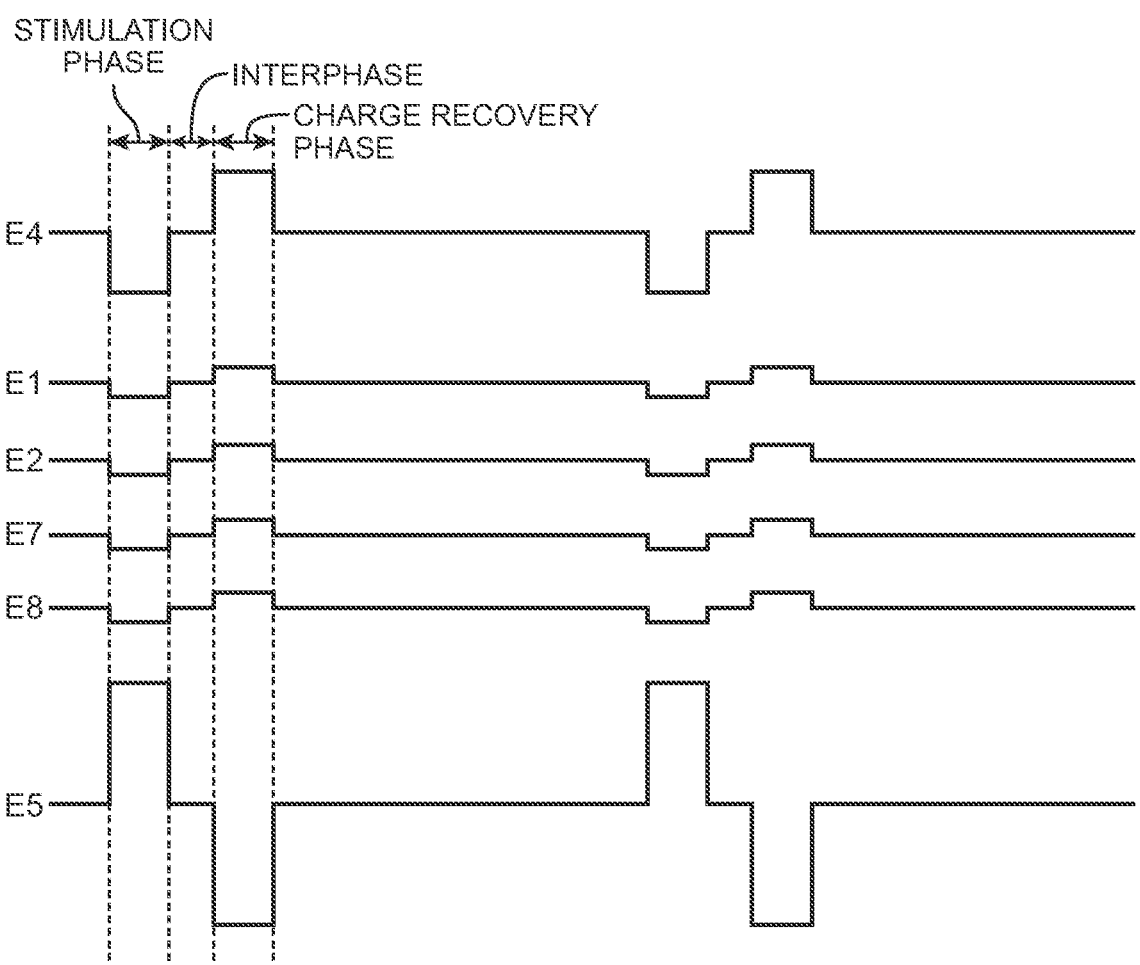
FIG. 12 is a timing diagram of another unconventional technique that the SCS system of FIG. 1 may use to stimulate tissue using the first phase of a bi-phasic pulse and both stimulate tissue and recover charge from the tissue using the second phase of the bi-phasic pulse.

In cases where there is a stimulation threshold differential between the stimulating electrodes, the possibility of discomfort due to excessive stimulation can occur. To avoid this problem, a portion of the electrical current that would otherwise flow through the lower threshold electrode or electrodes can be diverted to other electrodes. For example, if in the case above, electrode E4 has a stimulation threshold of 1 mA and electrode E5 has a stimulation threshold of 2 mA, then 2 mA of electrical current can be sourced from electrode E5, 1 mA of electrical current can be sunk to electrode E4, and 0.25 mA of electrical current can each be sunk to electrodes E1, E2, E7, and E8 during the first phase of each bi-phasic pulse, as shown in FIG. 12.

As a result, the target tissue region adjacent electrode E4 is stimulated with only 1 mA of cathodic electrical current during the first phase of each bi-phasic pulse. However, no tissue adjacent the other activated electrodes (namely, electrodes E1, E2, E5, E7, and E8) is stimulated during the first phase of each bi-phasic pulse. Notably, because the stimulation threshold for an anodic electrode is much greater than the stimulation threshold for a cathodic electrode, the target tissue region adjacent the first-phase anodic electrode E5 is not stimulated during the first phase even though 2 mA of electrical current flows through electrode E5. However, the target tissue region adjacent first-phase anodic electrode E5 is stimulated with 2 mA of cathodic electrical current during the charge recovery phase of each bi-phasic pulse, while no tissue is stimulated adjacent the other activated electrodes.

Figure 13:
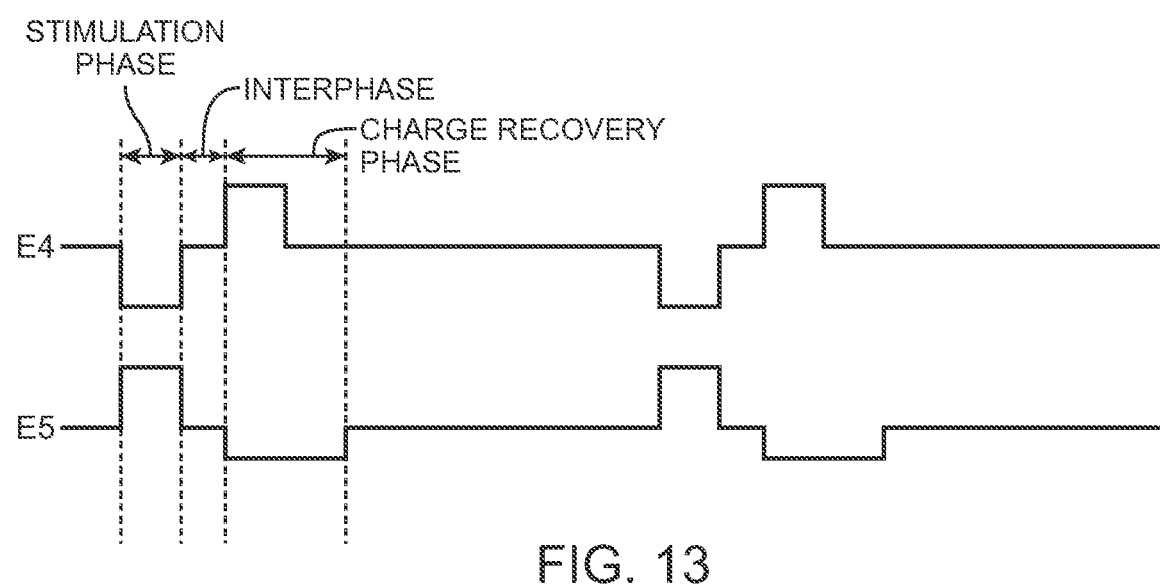
FIG. 13 is a timing diagram of still another unconventional technique that the SCS system of FIG. 1 may use to stimulate tissue using the first phase of a bi-phasic pulse and both stimulate tissue and recover charge from the tissue using the second phase of the bi-phasic pulse.

Another way to avoid the problem of over-stimulating tissue as a result of a stimulation threshold differential between stimulation electrodes is to modify the shape of the charge recover phase of each bi-phasic pulse. For example, if in the case where electrode E4 has a stimulation threshold of 2 mA and electrode E5 has a stimulation threshold of 1 mA, 2 mA of electrical current can be sourced from electrode E5, and 2 mA of electrical current can be sunk to electrode E4 during the first phase of each bi-phasic pulse. As a result, the first target tissue region adjacent electrode E4 is stimulated with 2 mA of cathodic electrical current during the first phase of each bi-phasic pulse. However, if a symmetrical bi-phasic pulse with a relatively long interphase is used, the 2 mA of cathodic electrical current sunk to electrode E5 during the second phase of each bi-phasic pulse would over-stimulate the second target tissue region adjacent electrode E5. However, as shown in FIG. 13, the duration of the second phase can be increased to thereby decrease the amplitude of the cathodic electrical current flowing through electrode E5 to 1 mA. As a result, proper stimulation of the target tissue region adjacent electrode E5 can be achieved during the second phase of each bi-phasic pulse.

The external control device may prompt the IPG 14 to sink electrical test currents to the respective electrodes E4, E5 in order to determine the stimulation thresholds of the respective electrodes. The external control device may determine the stimulation thresholds based on the test electrical currents (e.g., a perception threshold or a maximum comfortable threshold) in the manner described in U.S. Pat. No. 6,393,225, which is expressly incorporated herein by reference. The external control device can determine the stimulation thresholds of all electrodes for not only cathodic currents, but for anodic currents as well. The external control device can then process these stimulation thresholds to generate a table of possibilities for any given therapeutic electrode combination in a manner that prevents overstimulation by any of the electrodes.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A method of providing therapy to a patient using electrodes implanted in a patient, the electrodes including a first electrode, a second electrode and a third electrode implanted within the patient, the method comprising:
   generating an electrical waveform with a first phase and a second phase, wherein a first electrical current is provided by the first phase and a second electrical current is provided by the second phase;
   stimulating a first tissue region during the first phase of the electrical waveform by sourcing a portion of the first electrical current as anodic current from at least the second electrode and another portion of the first electrical current as anodic current from the third electrode and sinking at least a portion of the first electrical current as cathodic current to the first electrode; and
   stimulating a second tissue region during the second phase of the electrical waveform by sourcing a portion of the second electrical current as anodic current from the first electrode and another portion of the second electrical current anodic current from the third electrode and sinking at least a portion of the second electrical current as cathodic current to the second electrode during the second phase, wherein the sourcing the portion of the second electrical current as anodic current from the first electrode recovers at least a portion of injected charge during the first phase of the electrical waveform.

2. The method of claim 1, wherein
   a first tissue region adjacent to the first electrode has a first cathodic stimulation threshold for cathodic electrical current and a first anodic stimulation threshold for anodic electrical current, a second tissue region adjacent to the second electrode has a second cathodic stimulation threshold for cathodic electrical stimulation and a second anodic stimulation threshold for anodic electrical current, and a third tissue region adjacent to the third electrode has a third cathodic stimulation threshold for cathodic electrical stimulation and a third anodic stimulation threshold for anodic stimulation;
   the at least the portion of the first electrical current sunk as cathodic current to the first electrode is greater than the first cathodic stimulation threshold;
   the at least the portion of the second electrical current sunk as cathodic current to the second electrode is greater than the second cathodic stimulation threshold;
   the portion of the first electrical current sourced from the second electrode during the first phase is less than the second anodic stimulation threshold, and the portion of the second electrical current sourced from the first electrode during the second phase is less than the first anodic stimulation threshold.

3. The method of claim 2, wherein the second cathodic stimulation threshold is different from the first cathodic stimulation threshold.

4. The method of claim 3, wherein electrical current between the first and second electrodes during the first and second phase does not cause discomfort due to excessive stimulation of the first tissue region and the second tissue region.

5. The method of claim 4, further comprising performing at least one of the following steps:
   sinking another portion of the first electrical current to a fourth electrode implanted within the patient during the first phase if the first cathodic stimulation threshold for the first tissue region is less than the second cathodic stimulation threshold for the second tissue region; or
   sinking another portion of the second electrical current to the fourth electrode implanted within the patient during the second phase if the second cathodic stimulation threshold for the second tissue region is less than the first cathodic stimulation threshold for the first tissue region.

6. The method of claim 5, further comprising performing at least one of the following steps:
   adjusting the duration of the first phase to be longer than the duration of the second phase if the first stimulation threshold for the first tissue region is less than the second stimulation threshold for the second tissue region; and
   adjusting the duration of the second phase to be longer than the duration of the first phase if the second stimulation threshold for the second tissue region is less than the first stimulation threshold for the first tissue region.

7. The method of claim 2, wherein the other portion of the first electrical current sourced from the third electrode during the first phase is less than the third anodic stimulation threshold, and the other portion of the second electrical current sourced from the third electrode during the second phase is less than the third anodic stimulation threshold.

8. The method of claim 1, wherein the first and second tissue regions are contiguous.

9. The method of claim 1, wherein no electrical current is conveyed between the first electrode and the second electrode during a third phase between the first phase and the second phase.

10. The method of claim 9, wherein the third phase is at least one-half of the first phase.

11. The method of claim 9, wherein the combination of the first phase, second phase, and third phase form at least one bi-phasic pulse.

12. The method of claim 11, wherein the at least one bi-phasic pulse is symmetrical.

13. The method of claim 12, wherein the at least one bi-phasic pulse is asymmetrical.

14. The method of claim 1, wherein the stimulating the second tissue region includes:
   sinking another portion of the first electrical current to a third electrode implanted within the patient during the first phase of the electrical waveform, wherein a third tissue region adjacent the third electrode is not stimulated; and
   sourcing a third electrical current from the third electrode and sinking at least a portion of the third electrical current to the second electrode during the second phase of the electrical waveform, thereby, in combination with the at least a portion of the second electrical current sunk to the second electrode, recovering the at least a portion of the injected charge during the first phase of the electrical waveform.

15. The method of claim 1, wherein each of the first and second tissue regions comprises spinal cord tissue.

16. A method of providing therapy to a patient using first and second electrodes implanted within the patient, the method comprising:
   generating an electrical waveform with a first phase and a second phase;
   sourcing a first electrical current from the second electrode and sinking at least a portion of the first electrical current to the first electrode during the first phase to therapeutically stimulate a first tissue region adjacent the first electrode, the first tissue region having a first cathodic stimulation threshold;

sourcing a second electrical current from the first electrode and sinking at least a portion of the second electrical current to the second electrode during the second phase to recover at least a portion of the charge that had been injected into the patient during the first phase to stimulate a second tissue region adjacent the second electrode, the second tissue region having a second cathodic stimulation threshold different from the first cathodic stimulation threshold, wherein electrical current between the first and second electrodes during the first and second phase does not cause discomfort due to excessive stimulation of the first tissue region and the second tissue region; and performing at least one of the following steps:

sinking another portion of the first electrical current to a third electrode implanted within the patient during the first phase if the first cathodic stimulation threshold for the first tissue region is less than the second cathodic stimulation threshold for the second tissue region; and sinking another portion of the second electrical current to a third electrode implanted within the patient during the second phase if the second cathodic stimulation threshold for the second tissue region is less than the first cathodic stimulation threshold for the first tissue region.

17. The method of claim 16, further comprising performing at least one of the following steps:

adjusting the duration of the first phase to be longer than the duration of the second phase if the first cathodic stimulation threshold for the first tissue region is less than the second cathodic stimulation threshold for the second tissue region; and adjusting the duration of the second phase to be longer than the duration of the first phase if the second cathodic stimulation threshold for the second tissue region is less than the first cathodic stimulation threshold for the first tissue region.

18. The method of claim 16, wherein each of the first and second tissue regions comprises spinal cord tissue.

19. The method of claim 16, wherein no electrical current is conveyed between the first electrode and the second electrode during a third phase between the first phase and the second phase.

* * * * *